US009795441B2

(12) United States Patent
Fischell et al.

(10) Patent No.: US 9,795,441 B2
(45) Date of Patent: Oct. 24, 2017

(54) METHODS OF ABLATING TISSUE USING A CATHETER INJECTION SYSTEM

(71) Applicant: Ablative Solutions, Inc., Menlo Park, CA (US)

(72) Inventors: David R. Fischell, Menlo Park, CA (US); Tim A. Fischell, Kalamazoo, MI (US)

(73) Assignee: Ablative Solutions, Inc., Palo Alto, CA (US)

( * ) Notice: Subject to any disclaimer, the term of this patent is extended or adjusted under 35 U.S.C. 154(b) by 0 days.

(21) Appl. No.: 14/814,962

(22) Filed: Jul. 31, 2015

(65) Prior Publication Data

US 2015/0335384 A1    Nov. 26, 2015

Related U.S. Application Data

(60) Continuation of application No. 14/057,972, filed on Oct. 18, 2013, now Pat. No. 9,131,983, which is a
(Continued)

(51) Int. Cl.
*A61M 25/00* (2006.01)
*A61B 18/14* (2006.01)
(Continued)

(52) U.S. Cl.
CPC ........... *A61B 18/1492* (2013.01); *A61M 5/00* (2013.01); *A61B 2018/0022* (2013.01);
(Continued)

(58) Field of Classification Search
CPC ........ A61B 2017/00247; A61B 5/4839; A61B 5/4857; A61M 2025/0096; A61M 25/0084
(Continued)

(56) References Cited

U.S. PATENT DOCUMENTS

| 4,578,061 A | 3/1986 | Lemelson |
| 4,798,595 A | 1/1989 | Anderson et al. |

(Continued)

FOREIGN PATENT DOCUMENTS

| CN | 1147964 | 4/1997 |
| CN | 1494399 | 5/2004 |

(Continued)

OTHER PUBLICATIONS

U.S. Appl. No. 14/459,524, filed Jul. 14, 2014, Fischell et al.
(Continued)

*Primary Examiner* — Kevin C Sirmons
*Assistant Examiner* — Deanna K Hall
(74) *Attorney, Agent, or Firm* — Knobbe, Martens, Olson & Bear, LLP

(57) ABSTRACT

At the present time, physicians often treat patients with atrial fibrillation (AF) using radiofrequency (RF) catheter systems to ablate conducting tissue in the wall of the Left Atrium of the heart around the ostium of the pulmonary veins. These systems are expensive and take time consuming to use. The present invention circular ablation system CAS includes a multiplicity of expandable needles that can be expanded around a central axis and positioned to inject a fluid like ethanol to ablate conductive tissue in a ring around the ostium of a pulmonary vein quickly and without the need for expensive capital equipment. The expansion of the needles is accomplished by self-expanding or balloon expandable structures. The invention includes centering means so that the needles will be situated in a pattern surrounding the outside of the ostium of a vein. Also included are members that limit the distance of penetration of the needles into the wall of the left atrium. The present invention also has application to ablating tissue around the ostium of a renal artery for the treatment of hypertension.

22 Claims, 9 Drawing Sheets

Related U.S. Application Data division of application No. 13/092,363, filed on Apr. 22, 2011, now Pat. No. 8,663,190.

(51) Int. Cl.
*A61M 5/00* (2006.01)
*A61B 18/00* (2006.01)

(52) U.S. Cl.
CPC ............ *A61B 2018/00214* (2013.01); *A61B 2018/00375* (2013.01); *A61B 2018/00404* (2013.01); *A61B 2018/00434* (2013.01); *A61B 2018/00511* (2013.01); *A61B 2018/00577* (2013.01); *A61B 2018/143* (2013.01)

(58) Field of Classification Search
USPC ......................................................... 600/471
See application file for complete search history.

(56) References Cited

U.S. PATENT DOCUMENTS

| | | |
|---|---|---|
| 5,304,141 A | 4/1994 | Johnson et al. |
| 5,354,279 A | 10/1994 | Hofling |
| 5,385,562 A | 1/1995 | Adams et al. |
| 5,419,777 A | 5/1995 | Hofling |
| 5,464,395 A | 11/1995 | Faxon et al. |
| 5,474,102 A | 12/1995 | Lopez |
| 5,551,426 A | 9/1996 | Hummel et al. |
| 5,667,488 A | 9/1997 | Lundquist et al. |
| 5,672,173 A | 9/1997 | Gough |
| 5,683,384 A | 11/1997 | Gough |
| 5,713,863 A | 2/1998 | Vigil et al. |
| 5,792,094 A | 8/1998 | Stevens et al. |
| 5,855,576 A | 1/1999 | LeVeen et al. |
| 5,902,289 A | 5/1999 | Swartz et al. |
| 5,971,958 A | 10/1999 | Zhang |
| 5,980,516 A | 11/1999 | Mulier et al. |
| 6,056,744 A | 5/2000 | Edwards |
| 6,106,521 A | 8/2000 | Blewett et al. |
| 6,165,164 A | 12/2000 | Hill et al. |
| 6,190,353 B1 | 2/2001 | Makower et al. |
| 6,190,393 B1 | 2/2001 | Bevier et al. |
| 6,217,554 B1 | 4/2001 | Green |
| 6,221,049 B1 | 4/2001 | Selmon et al. |
| 6,231,591 B1 | 5/2001 | Desai |
| 6,254,599 B1 | 7/2001 | Lesh et al. |
| 6,277,107 B1 | 8/2001 | Lurie et al. |
| 6,283,947 B1 | 9/2001 | Mirzaee |
| 6,283,951 B1 | 9/2001 | Flaherty et al. |
| 6,302,870 B1 | 10/2001 | Jacobsen et al. |
| 6,375,660 B1 | 4/2002 | Fischell et al. |
| 6,432,092 B2 | 8/2002 | Miller |
| 6,478,778 B1 | 11/2002 | Jacobsen et al. |
| 6,514,248 B1 | 2/2003 | Eggers et al. |
| 6,547,803 B2 | 4/2003 | Seward et al. |
| 6,652,517 B1 | 11/2003 | Hall et al. |
| 6,685,648 B2 | 2/2004 | Flaherty et al. |
| 6,692,466 B1 | 2/2004 | Chow et al. |
| 6,764,461 B2 | 7/2004 | Mickley et al. |
| 6,854,467 B2 | 2/2005 | Boekstegers |
| 6,855,124 B1 | 2/2005 | Gonzalez et al. |
| 6,905,480 B2 | 6/2005 | McGuckin et al. |
| 6,966,897 B2 | 11/2005 | Shimazaki |
| 6,978,174 B2 | 12/2005 | Gelfand et al. |
| 6,997,903 B2 | 2/2006 | Wijay et al. |
| 7,015,253 B2 | 3/2006 | Escandon et al. |
| 7,056,286 B2 | 6/2006 | Ravenscroft et al. |
| 7,087,040 B2 | 8/2006 | McGuckin, Jr. et al. |
| 7,162,303 B2 | 1/2007 | Levin et al. |
| 7,273,469 B1 | 9/2007 | Chan et al. |
| 7,472,705 B2 | 1/2009 | Baran |
| 7,617,005 B2 | 11/2009 | Demarais et al. |
| 7,621,945 B2 | 11/2009 | Lennox et al. |
| 7,647,115 B2 | 1/2010 | Levin et al. |
| 7,653,438 B2 | 1/2010 | Deem et al. |
| 7,666,163 B2 | 2/2010 | Seward et al. |
| 7,691,080 B2 | 4/2010 | Seward et al. |
| 7,691,086 B2 | 4/2010 | Tkebuchava |
| 7,717,899 B2 | 5/2010 | Bowe et al. |
| 7,717,948 B2 | 5/2010 | Demarais et al. |
| 7,744,584 B2 | 6/2010 | Seward et al. |
| 7,756,583 B2 | 7/2010 | Demarais et al. |
| 7,794,444 B2 | 9/2010 | Lesh et al. |
| 7,850,656 B2 | 12/2010 | McKay et al. |
| 7,862,563 B1 | 1/2011 | Cosman et al. |
| 7,873,417 B2 | 1/2011 | Demarais et al. |
| 7,881,807 B2 | 2/2011 | Schaer |
| 7,942,854 B1 | 5/2011 | Von Oepen et al. |
| 8,000,764 B2 | 8/2011 | Rashidi |
| 8,100,883 B1 | 1/2012 | Johnson |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,758 B2 | 4/2012 | Chan et al. |
| 8,152,804 B2 | 4/2012 | Elmouelhi et al. |
| 8,175,711 B2 | 5/2012 | Demarais et al. |
| 8,396,548 B2 | 3/2013 | Perry et al. |
| 8,399,443 B2 | 3/2013 | Seward et al. |
| 8,465,451 B2 | 6/2013 | McRae et al. |
| 8,465,752 B2 | 6/2013 | Seward |
| 8,663,190 B2 | 3/2014 | Fischell et al. |
| 8,684,998 B2 | 4/2014 | Demarais et al. |
| 8,708,995 B2 | 4/2014 | Seward et al. |
| 8,740,849 B1 | 6/2014 | Fischell et al. |
| 8,771,252 B2 | 7/2014 | Gelfand et al. |
| 8,852,163 B2 | 10/2014 | Deem et al. |
| 8,948,865 B2 | 2/2015 | Zarins et al. |
| 8,975,233 B2 | 3/2015 | Stein et al. |
| 8,983,595 B2 | 3/2015 | Levin et al. |
| 9,011,879 B2 | 4/2015 | Seward |
| 9,056,185 B2 | 6/2015 | Fischell et al. |
| 9,131,983 B2 * | 9/2015 | Fischell ....................... 600/471 |
| 9,179,962 B2 | 11/2015 | Fischell et al. |
| 9,237,925 B2 | 1/2016 | Fischell et al. |
| 9,254,360 B2 | 2/2016 | Fischell et al. |
| 9,278,196 B2 | 3/2016 | Fischell et al. |
| 9,301,795 B2 | 4/2016 | Fischell et al. |
| 9,320,850 B2 | 4/2016 | Fischell et al. |
| 2001/0037065 A1 | 11/2001 | Graf et al. |
| 2002/0082584 A1 | 6/2002 | Rosenman et al. |
| 2002/0120238 A1 | 8/2002 | McGuckin et al. |
| 2002/0177846 A1 | 11/2002 | Mulier et al. |
| 2002/0183738 A1 | 12/2002 | Chee et al. |
| 2003/0032929 A1 | 2/2003 | McGuckin, Jr. |
| 2003/0171723 A1 | 9/2003 | Ponzi |
| 2004/0133154 A1 | 7/2004 | Flaherty et al. |
| 2004/0147902 A1 | 7/2004 | McGuckin, Jr. et al. |
| 2005/0070885 A1 | 3/2005 | Nobis et al. |
| 2005/0096647 A1 | 5/2005 | Steinke et al. |
| 2005/0187546 A1 | 8/2005 | Bek et al. |
| 2005/0234437 A1 | 10/2005 | Baxter et al. |
| 2005/0245923 A1 | 11/2005 | Christopherson et al. |
| 2005/0288730 A1 | 12/2005 | Deem et al. |
| 2006/0064065 A1 | 3/2006 | Russo |
| 2006/0173440 A1 | 8/2006 | Lamson et al. |
| 2006/0189940 A1 | 8/2006 | Kirsch |
| 2006/0271111 A1 | 11/2006 | Demarais et al. |
| 2007/0060812 A1 | 3/2007 | Harel et al. |
| 2007/0129720 A1 | 6/2007 | Demarais et al. |
| 2007/0129760 A1 | 6/2007 | Demarais et al. |
| 2007/0173899 A1 | 7/2007 | Levin et al. |
| 2007/0244479 A1 | 10/2007 | Beatty et al. |
| 2007/0270751 A1 | 11/2007 | Stangenes |
| 2007/0270757 A1 | 11/2007 | Willis et al. |
| 2008/0045890 A1 | 2/2008 | Seward et al. |
| 2008/0051756 A1 | 2/2008 | Makower et al. |
| 2008/0188812 A1 | 8/2008 | Valaie |
| 2008/0213331 A1 | 9/2008 | Gelfand et al. |
| 2008/0300454 A1 | 12/2008 | Goto |
| 2009/0018526 A1 | 1/2009 | Power |

(56) References Cited

U.S. PATENT DOCUMENTS

| | | |
|---|---|---|
| 2009/0018638 A1 | 1/2009 | Shirley et al. |
| 2009/0036948 A1 | 2/2009 | Levin et al. |
| 2009/0076500 A1 | 3/2009 | Azure |
| 2009/0312617 A1 | 12/2009 | Creed et al. |
| 2010/0076545 A1 | 3/2010 | Kleshinski et al. |
| 2010/0114087 A1 | 5/2010 | Edwards |
| 2010/0137860 A1 | 6/2010 | Demarais et al. |
| 2010/0137952 A1 | 6/2010 | Demarais et al. |
| 2010/0179416 A1 | 7/2010 | Hoey et al. |
| 2010/0191112 A1 | 7/2010 | Demarais et al. |
| 2010/0222851 A1 | 9/2010 | Deem et al. |
| 2010/0268307 A1 | 10/2010 | Demarais et al. |
| 2010/0305546 A1 | 12/2010 | Seward et al. |
| 2011/0009848 A1 | 1/2011 | Woodard et al. |
| 2011/0104060 A1 | 5/2011 | Seward |
| 2011/0104061 A1 | 5/2011 | Seward |
| 2011/0112400 A1 | 5/2011 | Emery et al. |
| 2011/0146674 A1 | 6/2011 | Roschak |
| 2011/0182912 A1 | 7/2011 | Evans et al. |
| 2011/0184337 A1 | 7/2011 | Evans et al. |
| 2011/0195971 A1 | 8/2011 | Cincotta |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257564 A1 | 10/2011 | Demarais et al. |
| 2011/0257622 A1 | 10/2011 | Salahieh et al. |
| 2012/0053604 A1 | 3/2012 | DiCaprio |
| 2012/0071832 A1 | 3/2012 | Bunch |
| 2012/0101490 A1 | 4/2012 | Smith |
| 2012/0108517 A1 | 5/2012 | Evans et al. |
| 2012/0116438 A1 | 5/2012 | Salahieh et al. |
| 2012/0130289 A1 | 5/2012 | Demarais et al. |
| 2012/0130345 A1 | 5/2012 | Levin et al. |
| 2012/0143181 A1 | 6/2012 | Demarais et al. |
| 2012/0197198 A1 | 8/2012 | Demarais et al. |
| 2012/0197252 A1 | 8/2012 | Deem et al. |
| 2012/0253186 A1 | 10/2012 | Simpson et al. |
| 2012/0253192 A1 | 10/2012 | Cressman |
| 2012/0271277 A1 | 10/2012 | Fischell et al. |
| 2012/0271301 A1 | 10/2012 | Fischell et al. |
| 2012/0296329 A1 | 11/2012 | Ng |
| 2013/0053792 A1 | 2/2013 | Fischell et al. |
| 2013/0053821 A1 | 2/2013 | Fischell et al. |
| 2013/0053822 A1 | 2/2013 | Fischell et al. |
| 2013/0090637 A1 | 4/2013 | Sliwa |
| 2013/0103026 A1 | 4/2013 | Kleshinski et al. |
| 2013/0131743 A1 | 5/2013 | Yamasaki et al. |
| 2013/0138082 A1 | 5/2013 | Salahieh et al. |
| 2013/0144251 A1 | 6/2013 | Sobotka |
| 2013/0178910 A1 | 7/2013 | Azamian et al. |
| 2013/0274614 A1 | 10/2013 | Shimada et al. |
| 2013/0274673 A1 | 10/2013 | Fischell et al. |
| 2013/0274674 A1 | 10/2013 | Fischell et al. |
| 2013/0287698 A1 | 10/2013 | Seward |
| 2014/0046298 A1 | 2/2014 | Fischell et al. |
| 2014/0121641 A1 | 5/2014 | Fischell et al. |
| 2014/0121644 A1 | 5/2014 | Fischell et al. |
| 2014/0236103 A1 | 8/2014 | Fischell et al. |
| 2014/0316351 A1 | 10/2014 | Fischell et al. |
| 2014/0358079 A1 | 12/2014 | Fischell et al. |
| 2014/0378906 A1 | 12/2014 | Fischell et al. |
| 2015/0005719 A1 | 1/2015 | Fischell et al. |
| 2015/0119674 A1 | 4/2015 | Fischell et al. |
| 2015/0119875 A1 | 4/2015 | Fischell et al. |
| 2015/0245863 A1 | 9/2015 | Fischell et al. |
| 2015/0335384 A1 | 11/2015 | Fischell et al. |
| 2015/0343156 A1 | 12/2015 | Fischell et al. |
| 2016/0045257 A1 | 2/2016 | Fischell et al. |
| 2016/0058489 A1 | 3/2016 | Fischell et al. |
| 2016/0120587 A1 | 5/2016 | Fischell et al. |
| 2016/0235464 A1 | 8/2016 | Fischell et al. |
| 2016/0242661 A1 | 8/2016 | Fischell et al. |
| 2016/0354137 A1 | 12/2016 | Fischell et al. |

FOREIGN PATENT DOCUMENTS

| | | |
|---|---|---|
| CN | 1927130 | 3/2007 |
| EP | 0834288 | 4/1998 |
| EP | 0876805 | 8/2006 |
| JP | H07-509389 | 10/1995 |
| JP | H08-89582 | 4/1996 |
| JP | 2001-527428 | 12/2001 |
| JP | 2002-510229 | 4/2002 |
| JP | 2002-542901 | 12/2002 |
| JP | 2004-516042 | 6/2004 |
| JP | 2005-40599 | 2/2005 |
| WO | WO 94/04220 | 3/1994 |
| WO | WO 95/13752 | 5/1995 |
| WO | WO 2004/030740 | 4/2004 |
| WO | WO 2010/124120 | 10/2010 |
| WO | WO 2011/094367 | 8/2011 |
| WO | WO 2012/145300 | 10/2012 |
| WO | WO 2012/145304 | 10/2012 |
| WO | WO 2013/028781 | 2/2013 |
| WO | WO 2013/159066 | 10/2013 |
| WO | WO 2014/070558 | 5/2014 |
| WO | WO 2015/061614 | 4/2015 |
| WO | WO 2015/168314 | 11/2015 |

OTHER PUBLICATIONS

U.S. Appl. No. 14/712,861, filed May 14, 2015, Fischell et al.
U.S. Appl. No. 14/738,776, filed Jun. 12, 2015, Fischell et al.
U.S. Appl. No. 14/814,962, filed Jul. 31, 2015, Fischell et al.
Angelini et al., Retractable-Needle Catheters: An Updated on Local Drug Delivery in Coronary Interventions, Texas Heart Institute Journal, 2008, p. 419-424.
Bello-Reuss et al., Effects of Acute Unilateral Renal Denervation in the Rat, J. of Clinical Investigation, vol. 56, Jul. 1975, p. 208-217.
Berne, Hemodynamics and Sodium Excretion of Denervated Kidney in Anesthetized and Unanesthetized Dog, Am. J. of Physiology, vol. 171, No. 1, Oct. 1952, p. 148-158.
Chinushi et al., "Blood Pressure and Autonomic Responses to Electrical Stimulation of the Renal Arterial Nerves Before and After Ablation of the Renal Artery", Hypertension, 2013, vol. 61, p. 450-456.
Dave, R.M., "The ClearWay™ RX Local Therapeutic Infusion Catheter", CathLab Digest, May 2010, vol. 18, No. 5, p. 1-6.
Dorward et al., "Reflex Responses to Baroreceptor, Chemoreceptor and Nociceptor Inputs in Single Renal Sympathetic Neurons in the Rabbit and the Effects of Anaesthesia on Them", Journal of the Autonomic Nervous System, 1987, vol. 18, p. 39-54.
Gado et al., "Intra-articular guanethidine injection for resistant shoulder pain: a preliminary double blind study of a novel approach" Annals of the Rheumatic Disease, 1996, p. 199-201.
Habara et al., "Novel Use of a Local Drug Delivery Catheter for Coronary Perforation", Journal of Invasive Cardiology, Jan. 2011, vol. 23, No. 1, p. 1-8.
Hamza et al., "Substantial Reduction in Single Sympathetic Nerve Firing After Renal Denervation in Patients With Resistant Hypertension", Nov. 19, 2012, p. 856-864.
Hsu et al., "The Use of Intravenous Guanethidine Block in the Management of Reflex Sympathtic Dystrophy Syndrome of the Hand." Second Congress of the Hong Kong Orthopaedic Association, Nov. 1982, p. 93-105.
Hering et al., "Substantial Reduction in Single Sympathetic Nerve Firing After Renal Denervation in Patients With Resistant Hypertension", Nov. 19, 2012 in 15 pages.
Klein et al. "Functional reinnervation and development of supersensitivity to NE after renal denervation in rats" American Physiological Society, 1980, p. 353-358.
Klein et al., Effect of Renal Denervation on Arterial Pressure and Renal Norepinephrine Concentration in Wistar-Kyota and Spontaneously Hypersensitive Rats, Can. J. Physiology and Pharmacology, vol. 58, 1980, p. 1384-1388.
Markovic, B., et al., "Embolization With Absolute Ethanol Injection of Insufficiently Ligated Renal Artery After Open Nephrectomy"; Diagnostic and Interventional Radiology, Mar. 2011; vol. 17, Issue 1, p. 88-91.

(56) References Cited

OTHER PUBLICATIONS

"Multi-prong Infusion Needle Case Study", from the web site of peridot™ Precision Manufacturing, http://www.peridotcorp.com/casestudy.aspx, Copyright 2012, in 8 pages.
Nanni et al., Control of Hypertension by Ethanol Renal Ablation (Radiology 148:51-54, Jul. 1983), p. 52-54.
Verloop et al., Eligibility for percutaneous renal denervation: the importance of a systematic screening, Journal of Hypertension, 2013, p. 1-7.
Vink et al. Limited destruction of renal nerves after catheter-based renal denervation: results of a human case study, Nephrol Dial Transplant, 2014, p. 1-3.
Zafonte et al., "Phenol and Alcohol Blocks for the Treatment of Spasticity", Physical medicine and rehabilitation clinics of North America, Nov. 2001, p. 817-832.
International Search Report and Written Opinion in PCT/US12/33918 mailed Sep. 6, 2012 in 15 pages.
International Search Report and Written Opinion in PCT/US12/33913 mailed Oct. 31, 2013 in 14 pages.
Extended Search Report in EP 12773575.1 mailed May 15, 2014 in 7 pages.
Office Action for Taiwan Patent Application 101114098 mailed Sep. 11, 2014 in 14 pages.
Office Action for Taiwan Patent Application 101114097 mailed Jun. 13, 2014 in 14 pages.
Demas et al., Novel method for localized, functional sympathetic nervous system denervation of peripheral tissue using guanethidine (Journal of Neuroscience Methods 112, 2001), p. 21-28.
Owens et al., Percutaneous Peri-Adventitial Guanethidine Delivery Induces Renal Artery Sympathectomy: Preclinical Experience and Implication for Refractory Hypertension (Journal of Vascular Surgery 53:17S), p. 87S.
Roytta et al., Taxol-induced neuropathy: short-term effects of local injection (Journal of Neurocytology 13, 1984), p. 685-701.
Trostel et al., Do renal nerves chronically influence renal function and arterial pressure in spinal rats? (The American Physiological Society 1992), p. 1265-1270.
U.S. Appl. No. 15/154,640, filed May 13, 2016, Fischell et al.

* cited by examiner

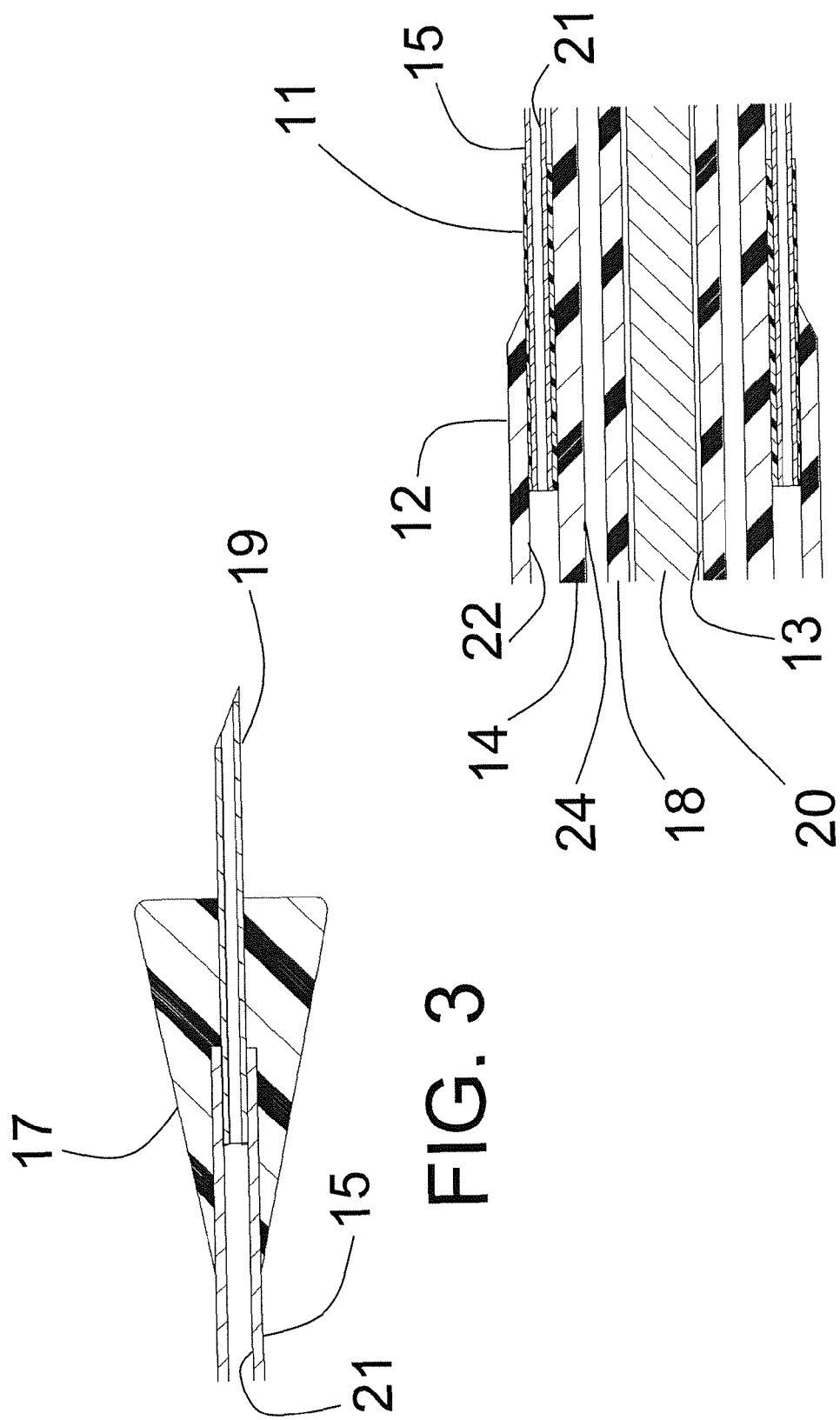

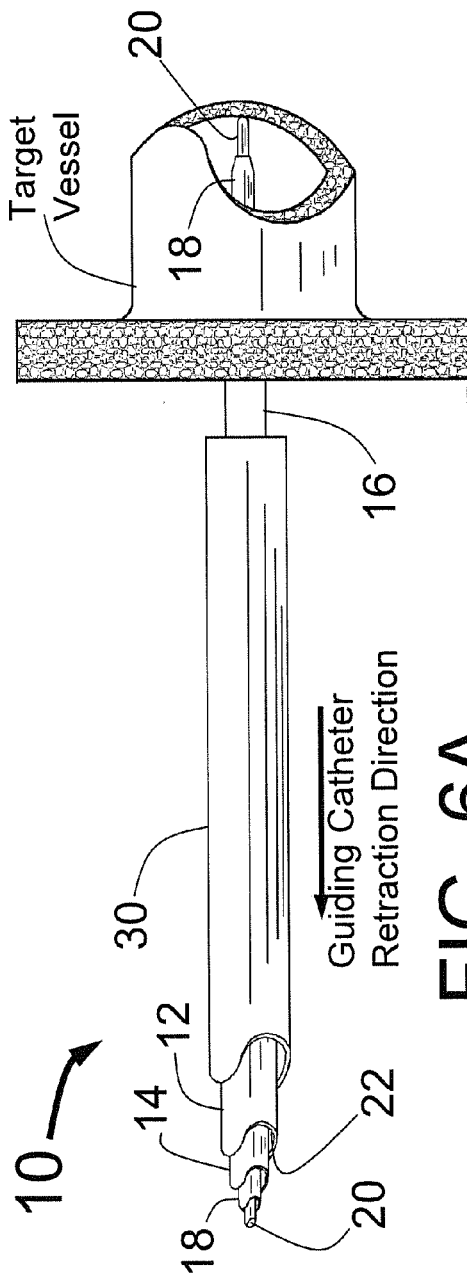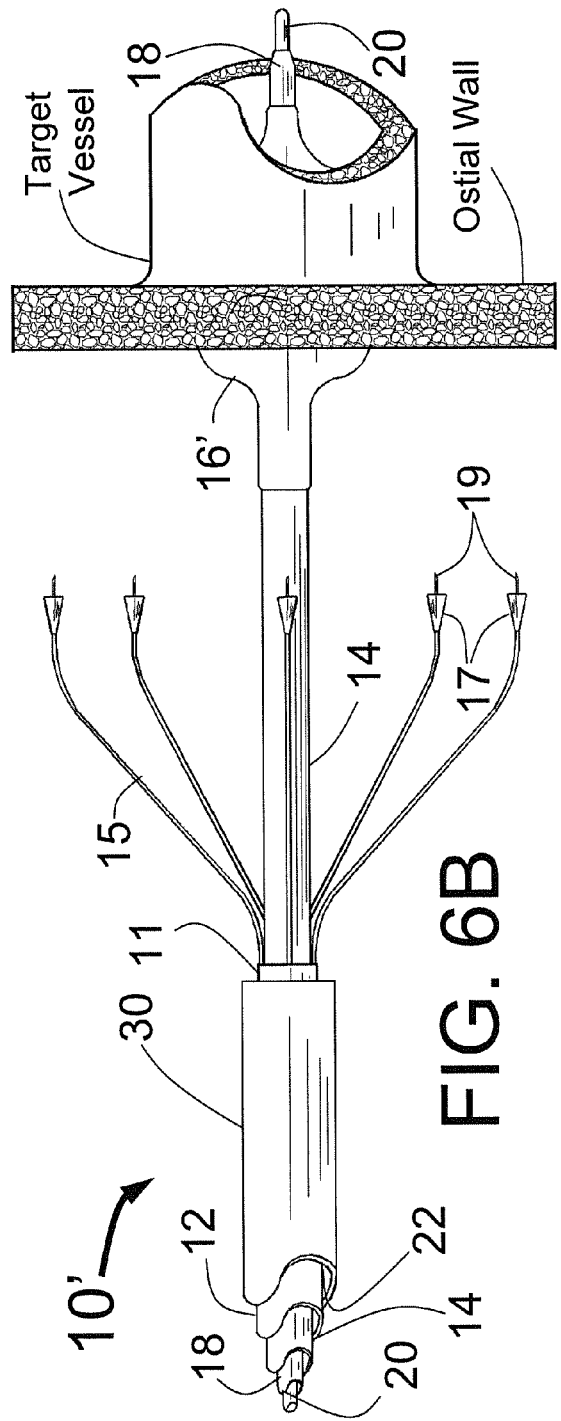

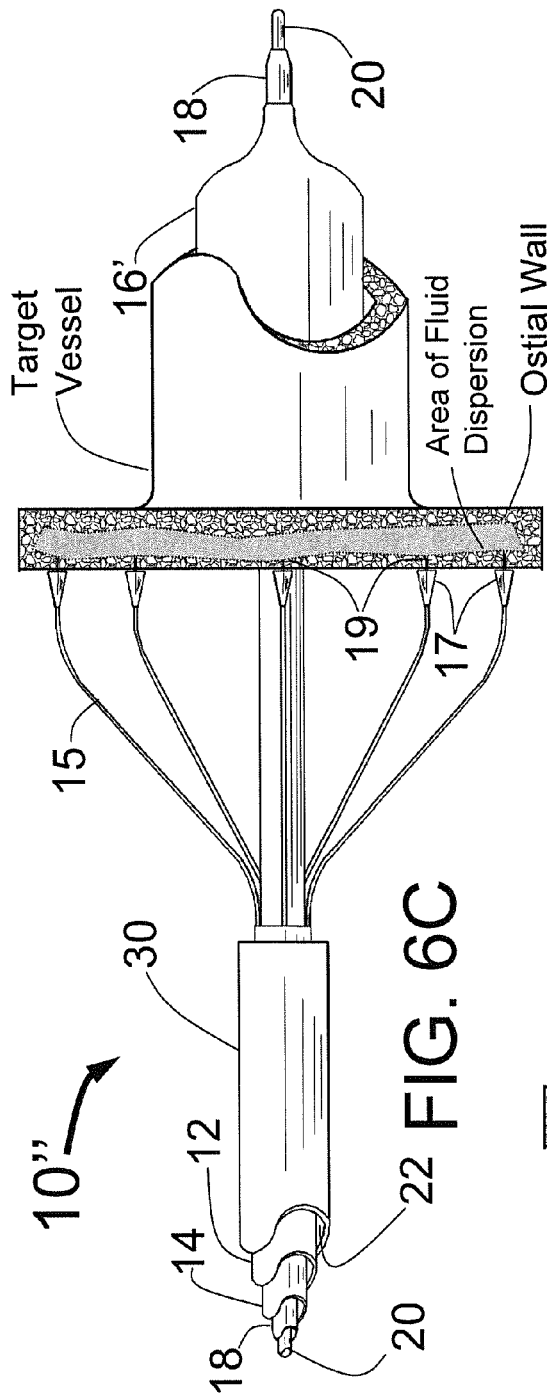
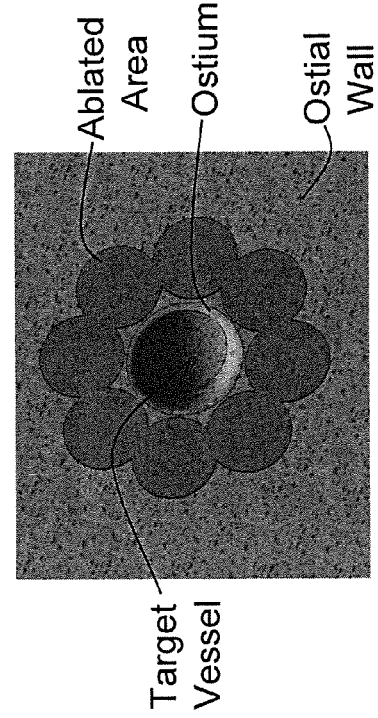
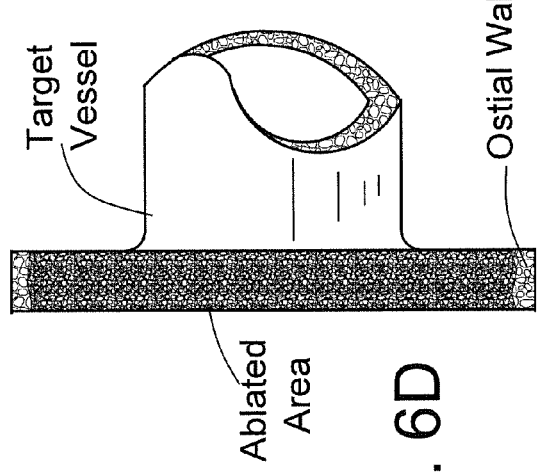
FIG. 6C
FIG. 6D
FIG. 6E

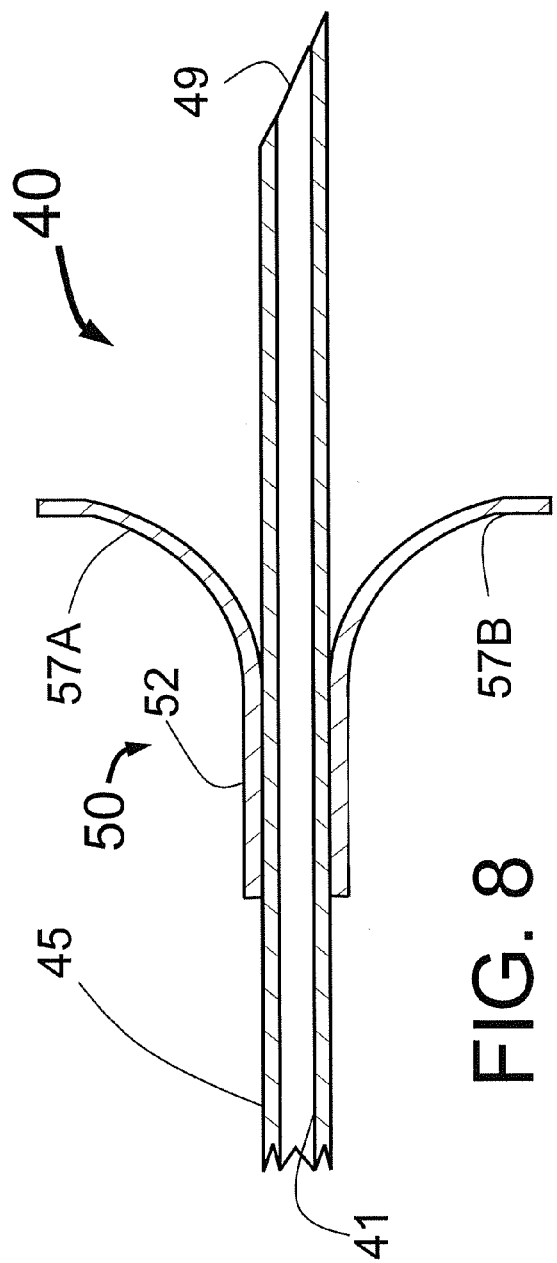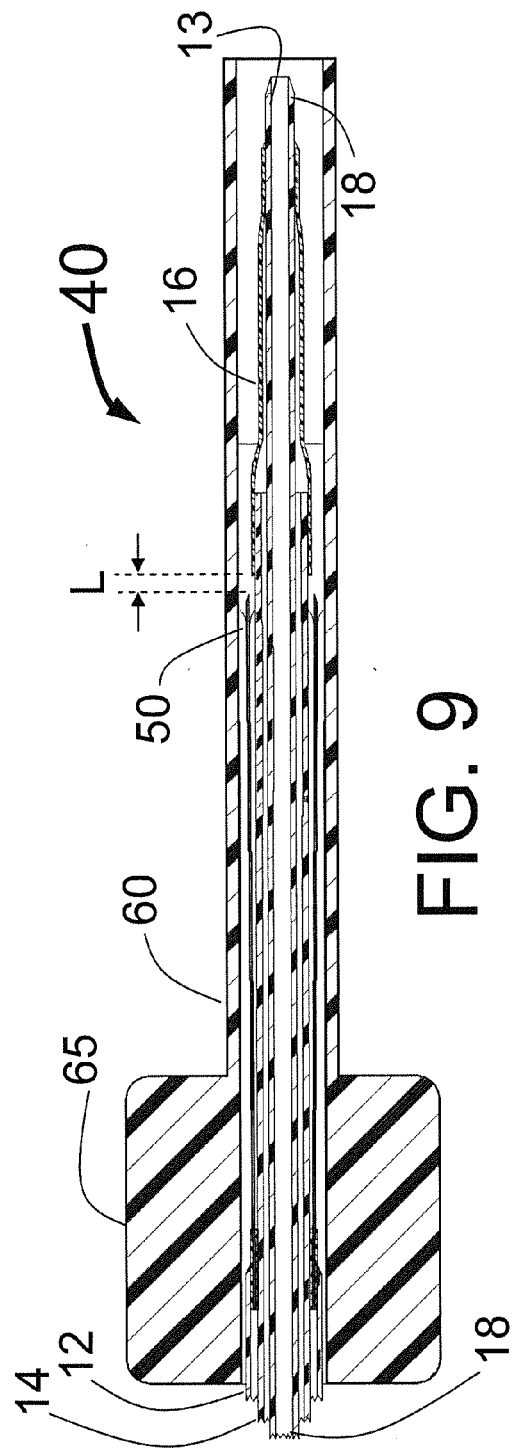
FIG. 8
FIG. 9

METHODS OF ABLATING TISSUE USING A CATHETER INJECTION SYSTEM

CROSS-REFERENCE TO RELATED APPLICATIONS

This application is a continuation of U.S. patent application Ser. No. 14/057,972, filed on Oct. 18, 2013, now issued as U.S. Pat. No. 9,131,983, which is a divisional of U.S. patent application Ser. No. 13/092,363, filed on Apr. 22, 2011, now issued as U.S. Pat. No. 8,663,190. The entirety of each of the foregoing applications is hereby incorporated by reference herein.

FIELD OF USE

This invention is in the field of devices to ablate muscle cells and nerve fibers for the treatment of cardiac arrhythmias and/or hypertension.

BACKGROUND OF THE INVENTION

At the present time, physicians often treat patients with atrial fibrillation (AF) using radio frequency (RF) catheter systems to ablate conducting tissue in the wall of the Left Atrium of the heart around the ostium of the pulmonary veins. Similar technology, using radiofrequency energy, has been used inside the renal arteries to ablate sympathetic and other nerve fibers that run in the wall of the aorta on the outside of the renal arteries, in order to treat high blood pressure. In both cases these are elaborate and expensive catheter systems that can cause thermal, cryoablative, or other injury to surrounding tissue. Many of these systems also require significant capital outlays for the reusable equipment that lies outside of the body, including RF generation systems and the fluid handling systems for cryoablative catheters.

Because of the similarities of anatomy, for the purposes of this disclosure, the term target vessel will refer here to either the pulmonary vein for AF ablation applications or the renal artery for hypertension therapy applications. The term ostial wall will refer to the wall of the Left Atrium surrounding a pulmonary vein for AF application and to the wall of the aorta for the hypertension application.

In the case of atrial fibrillation ablation, the ablation of tissue surrounding multiple pulmonary veins can be technically challenging and very time consuming. This is particularly so if one uses RF catheters that can only ablate one focus at a time. There is also a failure rate using these types of catheters for atrial fibrillation ablation. The failures of the current approaches are related to the challenges in creating reproducible circumferential ablation of tissue around the ostium (peri-ostial) of a pulmonary vein.

There are also potential risks using the current technologies for RF ablation to create sympathetic nerve denervation inside the renal artery for the treatment of hypertension. The long-term sequalae of applying RF energy inside the renal artery itself are unknown, but this could lead to late restenosis, embolization of debris into the renal parenchyma, or other problems inside the renal artery. There may also be uneven or incomplete sympathetic nerve ablation, particularly if there are anatomic abnormalities, or atherosclerotic or fibrotic disease inside the renal artery, such that there is nonhomogeneous delivery of RF energy. This could lead to treatment failures, or the need for additional and dangerous levels of RF energy to ablate the nerves that run along the adventitial plane of the renal artery. There are also significant safety issues with current technologies related to very long fluoroscopy and procedure times that lead to high levels of radiation exposure to both the patient and the operator, and may increase stroke risk in atrial fibrillation ablation.

Finally, while injection of ethanol as an ablative substance is used within the heart and other parts of the body, there has been no development of an ethanol injection system specifically designed for circular ablation of the ostial wall of a target vessel.

SUMMARY OF THE INVENTION

The present invention Circular Ablation System (CAS) is capable of producing damage in the tissue that surrounds the ostium of a blood vessel in a relatively short period of time using a disposable catheter requiring no additional capital equipment. The primary focus of use of CAS is in the treatment of cardiac arrhythmias and hypertension.

Specifically, there is a definite need for such a catheter system that is capable of highly efficient, and reproducible circumferential ablation of the muscle fibers and conductive tissue in the wall of the Left Atrium of the heart surrounding the ostium of the pulmonary veins which could interrupt atrial fibrillation (AF) and other cardiac arrhythmias.

This type of system may also have major advantages over other current technologies by allowing time efficient and safe circumferential ablation of the nerves in the wall of the aorta surrounding the renal artery (peri-ostial renal tissue) in order to damage the sympathetic nerve fibers that track from the peri-ostial aortic wall into the renal arteries, and thus improve the control and treatment of hypertension. Other potential applications of this approach may evolve over time.

The present invention is a catheter which includes multiple expandable injector tubes arranged circumferentially around the body of the CAS near its distal end. Each tube includes an injector needle at its distal end. There is a penetration limiting member proximal to the distal end of each needle so that the needles will only penetrate into the tissue of the ostial wall to a preset distance. This will reduce the likelihood of perforation of the ostial wall and will optimize the depth of injection for each application. The injector needles are in fluid communication with an injection lumen in the catheter body which is in fluid communication with an injection port at the proximal end of the CAS. Such an injection port would typically include a standard connector such as a Luer connector used to connect to a source of ablative fluid.

The expandable injector tubes may be self-expanding made of a springy material or a memory metal such as NITINOL or they may be expandable by mechanical means. For example, the expandable legs with distal injection needles could be mounted to the outside of an expandable balloon whose diameter is controllable by the pressure used to inflate the balloon.

The entire CAS is designed to be advanced over a guide wire in either an over the wire configuration where the guide wire lumen runs the entire length of the CAS or a rapid exchange configuration where the guide wire exits the catheter body at least 10 cm distal to the proximal end of the CAS and runs outside of the catheter shaft for its proximal section.

The distal end of the CAS also includes a centering means at or near its distal end. The centering means could be a mechanical structure or an expandable balloon. The centering means will help to ensure that the injector tubes will be engaged circumferentially around and outside of the ostium of the target vessel. If the injector tubes are expanded by a balloon, then it is envisioned that the distal portion of the balloon would have conical or cylindrical distal portions that would facilitate centering the CAS in the target vessel.

The CAS would also be typically packaged inside an insertion tube that constrains the self-expanding legs prior to insertion into a guiding catheter, and allows the distal end of the CAS to be inserted into the proximal end of a guiding catheter or introducer sheath.

The CAS might also be packaged to include an outer sheath that runs the entire length of the CAS so as to cover and protect the needles and also protect them from getting caught as the CAS is advanced distally to the desired location.

It is also envisioned that the injection needles could be formed from a radiopaque material such as tantalum or tungsten or coated with a radiopaque material such as gold or platinum so as to make them clearly visible using fluoroscopy.

It is also envisioned that one or more of the injector needles could be electrically connected to the proximal end of the CAS so as to also act as a diagnostic electrode(s) for evaluation of the electrical activity in the area of the ostial wall.

It is also envisioned that one could attach 2 or more of the expandable legs to an electrical or RF source to deliver electric current or RF energy around the circumference of a target vessel to the ostial wall to perform tissue ablation.

For use in the treatment of AF the present invention CAS would be used with the following steps:

Access to the left atrium via a large peripheral vein, such as the femoral vein, typically with the insertion of a sheath.

Use a trans septal approach to get into the left atrium, via the vein, to the right atrium, to enter the left atrium. This approach is a well known procedure.

Advance a guide wire and guiding catheter across the inter-atrial septum into the left atrium.

Using a guiding catheter with a shaped distal end or guiding sheath, engage the first targeted pulmonary vein. This can be confirmed with contrast injections as needed.

Advance a guide wire through the guiding catheter into the pulmonary vein.

Place the distal end of an insertion tube which constrains the distal end of the CAS into the proximal end of the guiding catheter.

Advance the distal end of the CAS into and advance the CAS through the guiding catheter, and tracking over the guidewire, until it is just proximal to the distal end of the guiding catheter.

Advance the CAS over the guidewire until the distal portion of its centering means is within the target vessel.

Expand the centering means. If the centering means is cylindrical, expand it until it is just slightly less (1-4 mm less) than the diameter of the target vessel. This will ensure that the catheter will be roughly "centered" within the target vessel to enable the circumferential deployment of the legs of the CAS around the target vessel ostium so that injection will be centered around the ostium of the target vessel.

Pull back the guiding catheter to leave space for the expanding injector tubes to open.

Expand the injector tubes or let them expand if they are self-expanding. If balloon expandable, adjust the balloon pressure to get the desired diameter. If self expanding, the circumference of the self-expansion can be adjusted in vivo by varying the distance of the pullback of the guiding catheter. That is, if one wants a smaller diameter (circumference) expansion to fit the ostial dimension of that specific target vessel, one can partially constrain the injector tube expansion by not fully retracting the guiding catheter all the way to the base of the tubes. However, the preferred method is to have the final opening distance be preset for the CAS, with the injector tubes fully expanded to their memory shape. Typically the CAS size would be pre-selected based on the anticipated or measured diameter of the ablation ring to be created, such that the fully expanded injector tubes create the correctly sized ablation "ring."

Advance the CAS until the injector needles at the distal end of the self-expanding injector tubes penetrate the ostial wall, with the penetration depth being a fixed distance limited by the penetration limiting member attached to each needle at a preset distance proximal to the distal end of the needle. If the centering means is conical, as the CAS is advanced distally, the cone will engage the ostium of the vein which will center the CAS.

Attach a syringe or injection system to the injection connector at the CAS proximal end.

Engagement of the ostial wall can be confirmed by injection of a small volume of iodinated contrast via a syringe, through the needles, prior to injection of the "ablative" fluid such as alcohol. If there is contrast "staining" of the tissue this will confirm that the needles are engaged into the tissue and not free floating in the left atrium or aorta.

Inject an appropriate volume of ethanol (ethyl alcohol) or other appropriate cytotoxic fluid from the syringe or injection system through the catheter and out of the needles into the ostial wall. A typical injection would be 1-10 ml. This should produce a multiplicity of circles of ablation (one for each needle) that will intersect to form an ablative ring around the ostium of the target vessel. Contrast could be added to the injection to allow x-ray visualization of the ablation area.

Once the injection is complete, retract the CAS back into the guiding catheter, which will collapse the self-expanding injector tubes. If the device is balloon expandable deflate the balloon and retract back into the guiding catheter.

In some cases, one may rotate the CAS 20-90 degrees and then repeat the injection if needed to make an even more definitive ring of ablation.

The same methods as per prior steps can be repeated to ablate tissue around the one or more of the other pulmonary veins during the same procedure, as indicated to ensure AF inhibition.

Remove the CAS from the guiding catheter completely.

When indicated, advance appropriate diagnostic electrophysiology catheters to confirm that the ablation has been successful.

Remove all remaining apparatus from the body.

A similar approach can be used with the CAS, via access from a peripheral artery such as the femoral artery, to treat hypertension, via ablation of tissue in the periostial aortic wall tissue surrounding one or both of the renal arteries, with the goal of ablating afferent and/or efferent sympathetic nerve fibers entering or exiting the kidney.

It is also envisioned that two or more of the legs/injector tubes may be connected to an electrical or RF field source to allow for electrical discharge or RF ablation to enable tissue ablation of the tissue in the ostial wall.

It is also envisioned that one could mount injector tubes with needles on the outer surface of an expandable balloon on the CAS in order to deliver 2 or more needles around the circumference of the ostium of a target vessel to inject ablative fluid to the ostial wall.

In this case, the distal portion of the balloon could include the centering means of a cylindrical or conical shape. This embodiment could also include an elastic band covering the injector tubes where the elastic band could both help maintain a smooth outer surface of the CAS to facilitate delivery as well as act as the penetration limiting member to limit the penetration of the injection needles.

Thus it is an object of the present invention CAS is to have a percutaneously delivered catheter that can be used to treat atrial fibrillation with a one, or more injections of an ablative fluid into the wall of the left atrium surrounding one or more pulmonary veins.

Another object of the present invention CAS is to have a percutaneously delivered catheter that can be used to treat hypertension with one, or more injections of an ablative fluid into the wall of the aorta surrounding a renal artery.

Still another object of the present invention CAS is to have a percutaneously delivered catheter that includes a multiplicity of circumferentially expandable injector tubes, each tube having a needle at its distal end for injection of an ablative fluid into the ostial wall of a target vessel.

Still another object of the present invention CAS is to have a centering means located at or near the catheter's distal end. The centering means designed to allow the injector to be centered on the target vessel so that the injected ablative fluid will form an ablative ring outside of the ostium of the target vessel. The centering means can be fixed or expandable, and may include a cylindrical or conical portion.

Another object of the invention is to have a penetration limiting member or means attached to the distal portion of the injector leg or as part of the distal portion of the CAS in order to limit the depth of needle penetration into the ostial wall.

Yet another object of the present invention CAS is to have one or more of the injector needles act as diagnostic electrodes for measurement of electrical activity within the ostial wall of the target vessel.

These and other objects and advantages of this invention will become obvious to a person of ordinary skill in this art upon reading of the detailed description of this invention including the associated drawings.

BRIEF DESCRIPTION OF THE DRAWINGS

FIG. 3 is a longitudinal cross sectional drawing showing area 3 of FIG. 2 which is the distal end of the self-expanding injector leg, injector needle and penetration limiter.

FIG. 4 is a longitudinal cross sectional drawing showing area 4 of FIG. 2 which is the proximal end of the self-expanding injector legs and how they are in fluid communication with the injection lumen of the CAS.

FIG. 6A is a three dimensional sketch showing the CAS with legs collapsed inside the distal end of a guiding catheter as the distal end of the CAS is inserted into the target vessel.

FIG. 6B is a three dimensional sketch showing the CAS after the CAS centering means has been expanded and the guiding catheter has been pulled back (retracted) allowing the self-expanding legs to expand.

FIG. 6C is a three dimensional sketch showing the CAS now advanced in the distal direction until the injector needles penetrate the ostial wall and the penetration limiters on each needle limit the penetration as they touch the ostial wall. In this configuration an ablative substance such as alcohol is injected into the ostial wall through the needles causing a complete circular ablation of tissue in the ostial wall in a ring surrounding the target vessel.

FIG. 6D shows target vessel and ostial wall after the CAS and guiding catheter have been removed from the body and the ablated tissue in the ostial wall remains.

FIG. 6E is a three dimensional sketch showing the overlapping area of ablation in the ostial wall that form a circle around the ostium of the target vessel.

FIG. 8 is a longitudinal cross sectional drawing of an alternative version of the injector needle and penetration limiting means.

FIG. 9 is a longitudinal cross section of the CAS with the injector needle of FIG. 8 with the injector tubes shown collapsed inside the introducer tube used to insert the CAS into the proximal end of a guiding catheter or sheath.

DETAILED DESCRIPTION OF THE PREFERRED EMBODIMENT

Figure 1:
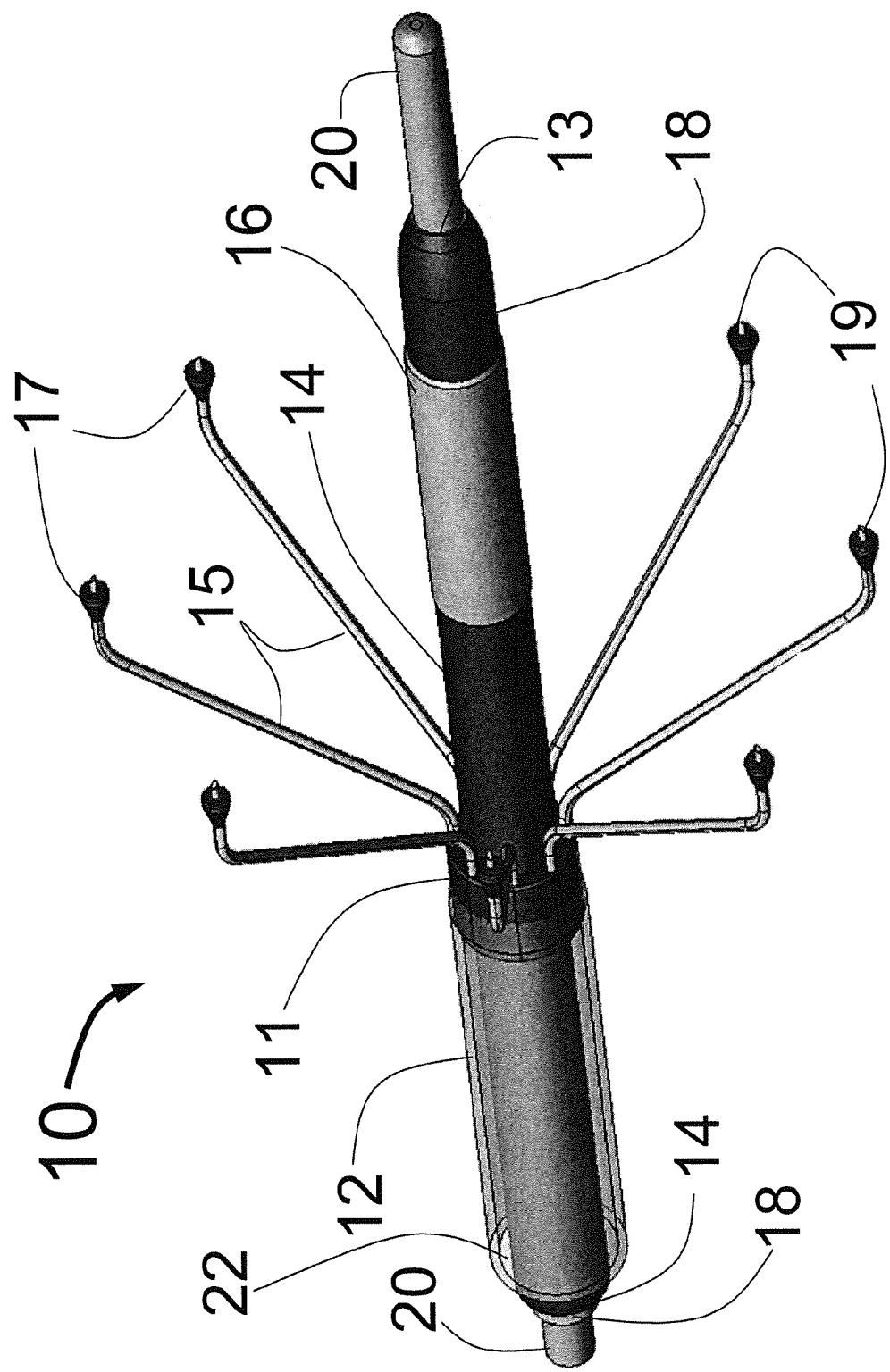
FIG. 1 is a three dimensional sketch of the distal end of the present invention Circular Ablation System (CAS).

FIG. 1 is a three dimensional sketch of the distal end of the present invention Circular Ablation System (CAS) 10 in its state before it is loaded into a guiding catheter or sheath for delivery over the guide wire 20 into a human being. The proximal portion of the CAS 10 includes three tubes, an outer tube 12, a middle tube 14 and an inner tube 18. The guidewire 20 can be slidably advanced or removed through the guide wire lumen 13 inside of the inner tube 18. An expandable cylindrical balloon 16 is attached at its proximal end to the middle tube 14 and at its distal end to the inner tube 18. The balloon inflation lumen is located between the inner tube 18 and the middle tube 14. The balloon 16 can be inflated by injection of a fluid through the balloon inflation lumen and deflated by applying suction to the balloon inflation lumen.

A injector transition manifold 11 is sealed onto the outside of the middle tube 14. The outer tube 12 is sealed at its distal end onto the outside of the injector transition manifold 11. The expandable injector tubes 15 are attached at their proximal end to or through the injector transition manifold 11 so that the proximal lumen of the injector tubes 15 are in fluid communication with the fluid injection lumen 22 that lies between the middle tube 14 and the outer tube 12. The injector tubes 15 could be made of a springy metal such as L605 or the preferred embodiment being made from a memory metal such as NITINOL. A plastic hub 17 is attached to the distal end of each injector tube 15. An injector needle 19 extends distally from the distal end of each plastic hub 17. The lumen of each injector needle 19 is in fluid communication with the lumen of the expandable injector tube (leg) 15. Each hub 17 acts as a penetration limiting member to limit the penetration of the distally attached needle 19 into the ostial wall of the target vessel. In this embodiment it is envisioned that the penetration of the needles 19 would be limited to pre-set distance, for example the distance might be between 0.5 mm and 1 cm.

Figure 2:
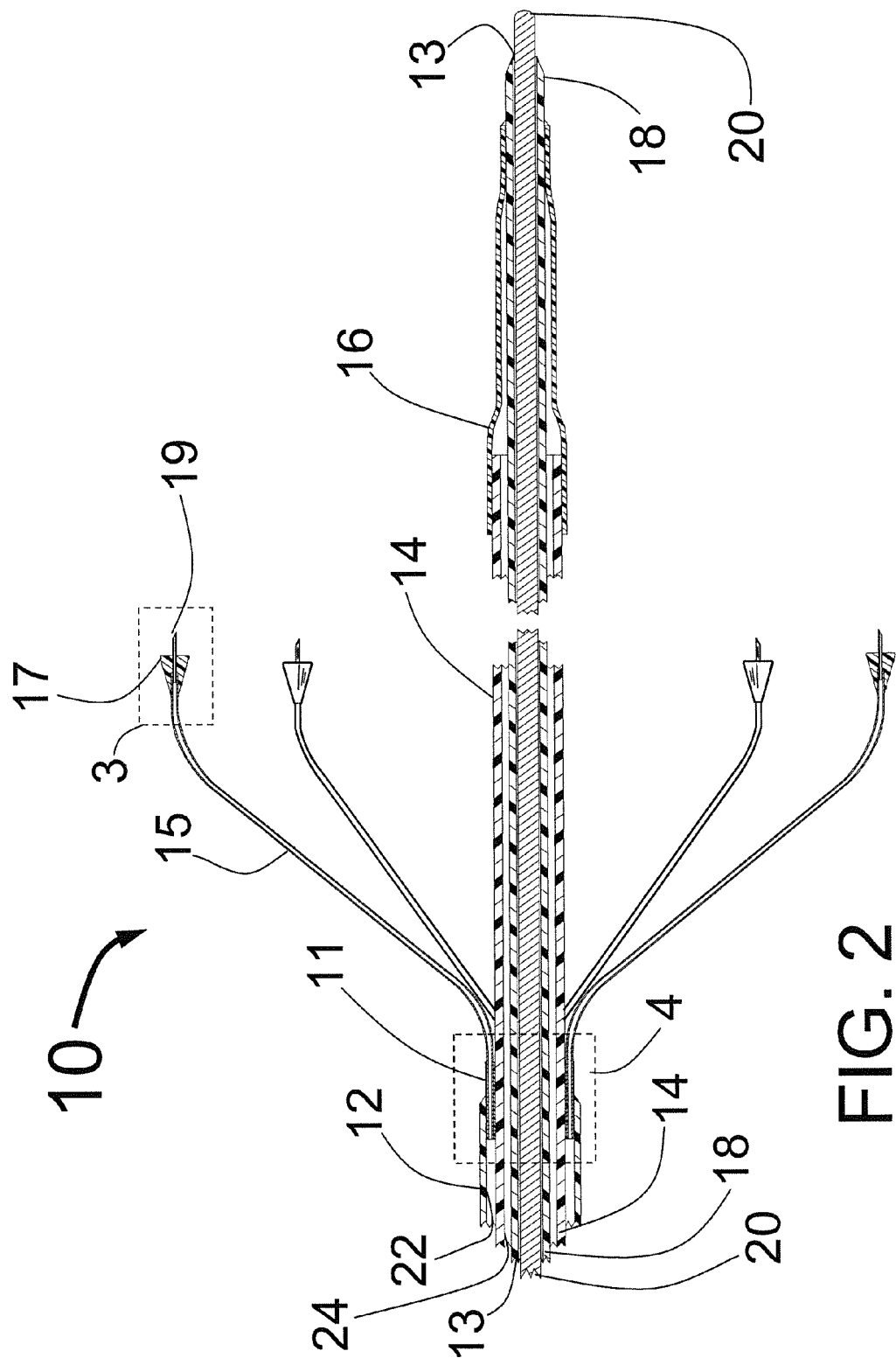
FIG. 2 is a longitudinal cross sectional drawing of the distal end of the CAS.

FIG. 2 is a longitudinal cross sectional drawing of the distal end of the CAS 10 in its state before it is loaded into a guiding catheter or sheath for delivery over the guide wire 20 into a human being. The proximal portion of the CAS 10 includes three tubes, an outer tube 12, a middle tube 14 and an inner tube 18. The guidewire 20 can be advanced or removed through the guide wire lumen 13 inside of the inner tube 18. An expandable cylindrical balloon 16 is attached at its proximal end to the middle tube 14 and at its distal end to the inner tube 18. The balloon 16 may be either an elastic balloon or a folded inelastic balloon such as is used for angioplasty. The proximal end of the balloon 16 is attached to the middle tube 14 and the distal end of the balloon 16 is attached to the inner tube 18 such that the area under the balloon 16 is in fluid communication with the balloon inflation lumen 24 that lies between the middle tube 14 and the inner tube 18. The balloon 16 can be inflated by injection of a fluid or gas through the balloon inflation lumen 24 and deflated by applying suction to the balloon inflation lumen 24. Normal saline solution including a fluoroscopic contrast agent would be the typical fluid used to inflate the balloon 16.

The injector transition manifold 11 is sealed onto the outside of the middle tube 14. The outer tube 12 is sealed at its distal end onto the outside of the injector transition manifold 11. The expandable injector tubes 15 are attached at their proximal end through the injector transition manifold 11 so that the proximal lumen of the injector tubes 15 are in fluid communication with the fluid injection lumen 22 that lies between the middle tube 14 and the outer tube 12. FIG. 4 shows an expanded version of the area 4 of FIG. 2. The injector tubes 15 could be made of a springy metal such as L605 or the preferred embodiment being made from a memory metal such as NITINOL. A plastic hub penetration limiter 17 with flattened distal end to act as a means of limiting the penetration of the needle 19 is attached over the distal end of each of the 8 expandable injector tubes 15. An injector needle 19 extends distally from the distal end of each plastic hub 17. The lumen of each injector needle is in fluid communication with the lumen of the expandable injector tube 15.

FIG. 3 is an enlarged longitudinal cross sectional drawing showing area 3 of FIG. 2 which is the distal end of the self-expanding injector tube 15 with injector tube lumen 21, injector needle 19 and penetration limiter 17. While FIG. 3 shows the limiters 17 as being symmetric around the injector tube 15, it is also envisioned that an asymmetric penetration limiter, for example a limiter with significant material only on the inside might be preferable as it would be less likely to catch on a guiding catheter when the CAS 10 is advanced through or retracted back into the guiding catheter at the end of the procedure.

FIG. 4 is an enlarged longitudinal cross sectional drawing of the CAS 10 showing area 4 of FIG. 2 which is the proximal end of the self-expanding injector tubes 15 with lumens 21. FIG. 4 shows detail on how the lumens 21 of the injector tubes 15 are in fluid communication with the injection lumen 22 of the CAS 10. Specifically, the proximal section of each injector tube 15 is inserted through a hole in the injector transition manifold 11 and fixedly attached and sealed to the manifold 11 so that the proximal end of the each tube 15 has its proximal end and opening in fluid communication with the injector lumen 22 that lies between the outer tube 12 and the middle tube 14 of the CAS 10. As another way of achieving this structure it is also conceived that the injector manifold 11 might be a single piece of plastic molded over the proximal ends of the injector tubes 15 in a molding operation prior to assembly.

Figure 5:
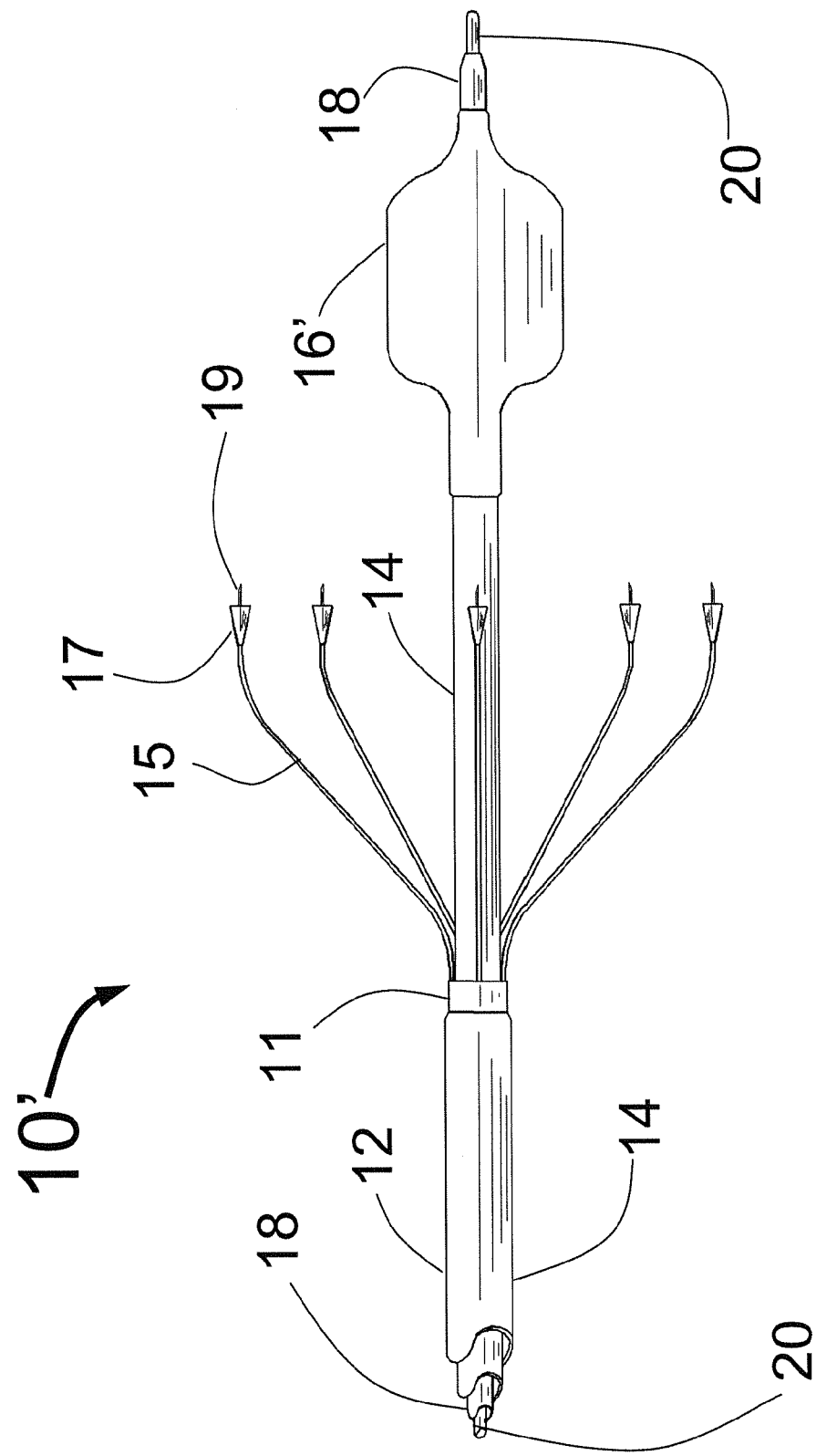
FIG. 5 is a three dimensional sketch showing the CAS with centering balloon expanded.

FIG. 5 shows a three dimensional sketch showing the CAS 10' with centering balloon 16' expanded. Also shown are the outer tube 12, middle tube 11 and inner tube 18 with guidewire 20. The injector tubes 15 protrude in the distal direction from the distal end of the injector manifold 11 and have hubs 17 (penetration limiting members) with injector needles 19 at their distal end. The expanded balloon 16' should be inflated to be just slightly less than the diameter of the target vessel. This will allow it to act as a centering means without causing undue injury to the target vessel wall. Ideally, the balloon 16' would be a low pressure elastic balloon where the diameter can be adjusted by using the appropriate pressure to inflate the balloon 16' through the balloon inflation lumen 24. It is also conceived that the CAS 10' would have a non-compliant or semicompliant molded folded balloon with a limited diameter range vs. pressure such as is used in an angioplasty balloons.

FIG. 6A is a three dimensional sketch showing the CAS 10 with injector tubes 15 collapsed inside the distal end of a guiding catheter 30 as the distal end of the CAS 10' is inserted into the target vessel over the guide wire 20. The distal end of the guiding catheter 30 would normally first be placed inside of the ostium of the target vessel (engaged) and is shown here slightly back from the ostium as it would be during the first part of its distal retraction. From the position shown in FIG. 6A, the guiding catheter 30 is pulled back (retracted) in the proximal direction allowing the self expanding injector tubes 15 to spring open to their open position. The extent of leg expansion could be adjusted (limited and smaller) in vivo by not fully retracting the guiding catheter, thus modestly constraining the expanded dimension of the expandable tubes 15.

FIG. 6B is a three dimensional sketch showing the CAS 10' after the guiding catheter has been pulled back and the inflatable balloon 16' has been expanded with the guide wire 20 still lying within the target vessel. From this state, the CAS 10' with expanded balloon 16' is advanced in the distal direction until the needles 19 penetrate the ostial wall surrounding the target vessel. Engagement of the ostial wall could be confirmed by injection of a small volume of iodinated contrast through the needles, prior to injection of the "ablative" fluid such as alcohol.

FIG. 6C is a three dimensional sketch showing the CAS 10" now advanced in the distal direction with the injector needles 19 fully penetrating the ostial wall and the penetration limiting members (hubs) 17 on each needle limiting the penetration as they touch the ostial wall. In this configuration an ablative substance such as ethanol is injected into the ostial wall through the needles 19. The ablative fluid will disperse from the needles and as more ablative fluid is injected, the area of fluid dispersion shown in FIG. 6C will increase so as to eventually cause a complete circular ablation of tissue in the ostial wall in a ring surrounding the target vessel. The balloon 16' is then deflated and the CAS 10 is pulled back in the proximal direction until the needles 19 are no longer penetrating the ostial wall. The CAS 10 is then pulled back more in the proximal direction into the distal end of the guiding catheter 30 which will collapse the self expanding injector tubes 15. At this point the guide wire 20 may be advanced into another target vessel and the ablation procedure repeated. After the last target vessel is treated, the CAS 10 can then be removed from the patient's body. At this point electrophysiology catheters may be introduced through the guiding catheter to verify the success of the procedure.

FIG. 6D shows target vessel and ostial wall after the CAS 10 and guiding catheter have been removed from the body and the ablated tissue in the ostial wall remains.

FIG. 6E is a three dimensional sketch showing a representation of the overlapping areas of ablation in the ostial wall from each needle 19 that form a ring around the ostium of the target vessel after the procedure using the CAS 10 has been completed. While FIG. 6E shows overlapping circles to highlight the ablation from each needle 19, in reality because ethanol disperses readily in tissue, the circles would actually blend together.

Figure 7:
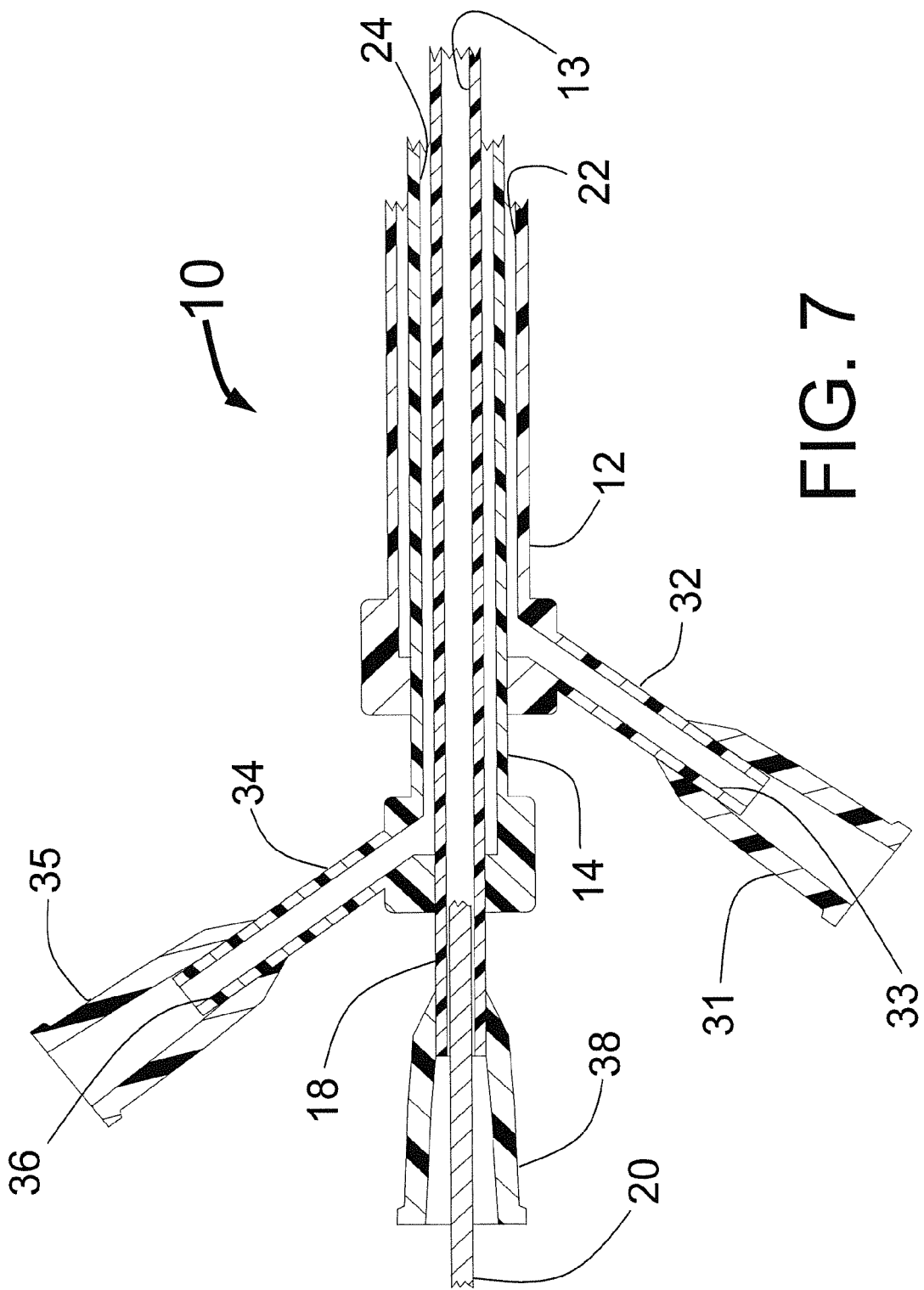
FIG. 7 is a longitudinal cross sectional drawing of the proximal end of the present invention CAS.

FIG. 7 is a longitudinal cross sectional drawing of the proximal end of the present invention CAS 10. The proximal end of the inner tube 18 is attached to a Luer fitting 38 that can be used to inject fluid to flush the guide wire lumen 13 inside of the inner tube 18. The guide wire 20 is inserted through the guide wire lumen 13. The proximal end of the middle tube 14 is attached to the side tube 34 with lumen 36. The proximal end of the side tube 34 is attached to the Luer fitting 36 which can be attached to a syringe or balloon inflation device to inflate and deflate the balloon 16 of FIGS. 1 and 2. The lumen 36 is in fluid communication with the balloon inflation lumen 24 that lies between the middle tube 14 and the inner tube 18. The proximal end of the outer tube 12 is connected to the distal end of the side tube 32 with lumen 33. The side tube 32 is connected at its proximal end to the Luer fitting 31 that can be connected to a syringe or fluid injector to inject an ablative substance such as ethanol through the lumen 33 into the injection lumen 22 through the injector tubes 15 and out the needles 19 into the ostial wall of the target vessel. Additional valves and stopcocks may also be attached to the Luer fittings 35 and 31 as needed.

FIG. 8 is a longitudinal cross sectional drawing of an alternative version of the injector needle 49 of the CAS 40 with two differences from that shown in FIG. 3. First, here the injector needle 49 is the sharpened distal end of the self-expanding tube 45 with injector tube lumen 41 while in FIG. 3 the self-expanding tube 15 was attached to a separate injector needle 19 with lumen 21. The penetration limiting means of this embodiment is the limiter 50 with tubular section 52 that is attached to the outside of the tube 45 with self-expanding legs 57A and 57B that will open up as the CAS 40 is deployed. The limiter 50 would typically be made from a single piece of NITINOL preset into the shape shown with at least 2 self-expanding legs. The major advantage if this design is that the penetration limiting means takes up very little space within the guiding catheter used for device delivery making it easier to slide the CAS 40 through the guiding catheter. Although two legs 57A and 57B are shown it is conceived that 1, 3, 4 or more legs could be attached to the tube 45 to act as a penetration limiting member or means when the needle 49 is advanced to penetrate the ostial wall of the target vessel.

FIG. 9 is a longitudinal cross section of the distal portion of the CAS 40 with the injector needle 49 and limiter 50 of FIG. 8 with the injector tubes 45 shown collapsed inside an insertion tube 60 with handle 65 used to insert the CAS 40 into the proximal end of a guiding catheter or sheath. This is how the CAS 40 would be typically packaged although the insertion tube 60 might be packaged proximal to the injector tubes 15 where the insertion tube 60 would be slid in the distal direction to collapse the injector tubes 15 just before the CAS 40 is inserted in the guiding catheter or sheath. Such an insertion tube 60 could be used with all of the embodiments of the present invention disclosed herein. The steps to prepare it for use would be as follows:

1. Remove the sterilized CAS 40 from its packaging in a sterile field.
2. Flush the guide wire lumen 13 with saline solution.
3. Access to the left atrium via a large peripheral vein, such as the femoral vein, typically with the insertion of a sheath.
4. Use a trans septal approach to get into the left atrium, via the vein, to the right atrium, to enter the left atrium. This approach is a well known procedure.
5. Advance a guide wire and guiding catheter across the inter-atrial septum into the left atrium.
6. Using a guiding catheter or guiding sheath with a shaped distal end, engage the first targeted pulmonary vein. This can be confirmed with contrast injections as needed.
7. Advance a guide wire through the guiding catheter into the pulmonary vein.
8. Insert the proximal end of the guide wire into the guide wire lumen 13 of the CAS 40 and bring the wire through the CAS 40 and out the proximal end Luer fitting 38 of FIG. 7.
9. Place the distal end of an insertion tube 60 which constrains the distal end of the CAS 40 into the proximal end of the guiding catheter. There is typically a TuohyBorst fitting attached to the distal end of a guiding catheter to constrain blood loss. The insertion tube 60 can be pushed through the opened Tuohy-Borst fitting and the Tuohy-Borst fitting closed on its outside to hold it in place.
10. Advance the distal end of the CAS 40 out of the insertion tube 60 and into the guiding catheter.
11. Advance the CAS 40 (or 10) through the guiding catheter 30 of FIG. 6A, and tracking over the guide wire 20, until the unexpanded tubes 45 (or 15) are located just proximal to the distal end of the guiding catheter 30. This is shown in FIG. 6A.
12. Advance the CAS 40 or 10 over the guide wire 20 until the balloon 16 used for centering is within the target vessel.
13. Expand the balloon 16 used for centering until it is just slightly less (1-4 mm less) than the diameter of the target vessel. This will ensure that the distal portion of the CAS 40 or 10 will be roughly "centered" within the target vessel to enable the circumferential deployment of the expandable tubes 45 or 15 centered around the target vessel ostium so that injection into the ostial wall will be centered around the ostium of the target vessel.
14. Pull back the guiding catheter 30 so that the self-expanding injector tubes 15 open. The circumference of the tube 15 expansion can be adjusted in vivo by varying the distance of the pullback of the guiding catheter 30. That is, if one wants a smaller diameter (circumference) of expansion to fit the ostial dimension of that specific target vessel, one can partially constrain the injector tube 15 expansion by not fully retracting the guiding catheter 30 beyond the proximal end of the injector tubes 15. However, the preferred method is to have the final opening distance be preset for the CAS 40 or 10, with the injector tubes 45 (or 15) fully expanded to their maximum diameter governed by their memory shape. Typically the CAS 40 or 10 maximum diameter of the injector tubes 15 would be pre-selected based on the anticipated or measured diameter of the ablation ring to be created, such that the fully expanded injector tubes create the correctly sized ablation "ring." This step is portrayed in FIG. 6B.

15. Advance the CAS 40 or 10 until the injector needles in the self-expanding injector tubes 45 (or 15) penetrate the ostial wall, as seen in FIG. 6C with the penetration depth being a fixed distance limited by the penetration limiting members 17 of FIG. 6C or 50 of FIGS. 8 and 9.
16. Attach a syringe or injection system to the Luer fitting 35 of FIG. 7.
17. Prior to injection of the "ablative" fluid such as alcohol engagement of the ostial wall could be confirmed by injection of a small volume of iodinated contrast via a syringe through the Luer fitting 35 and out of the needles 49 or 19 of FIG. 6C. If there is contrast "staining" of the tissue this will confirm that the needles 49 or 19 are engaged into the tissue and not free floating in the left atrium or aorta.
18. Inject an appropriate volume of ethanol (ethyl alcohol) or other appropriate cytotoxic fluid from the syringe or injection system through the catheter and out of the needles 49 or 19 into the ostial wall. A typical injection would be 1-10 ml. This should produce a multiplicity of interlocking circles of ablation (one for each needle) that will run together and intersect to form a ring or ablated tissue around the ostium of the target vessel as is seen in FIG. 6E.
19. In some cases, one may rotate the CAS 20-90 degrees and then repeat the injection to make an even more definitive ring of ablation.
20. Retract the CAS 40 or 10 back into the guiding catheter 30 which will collapse the self-expanding injector tubes 45 or 15.
21. The same methods as per steps 6-19 can be repeated to ablate tissue around the one or more of the other pulmonary veins during the same procedure, as indicated to ensure AF ablation or the 2nd Renal artery in the treatment of hypertension.
22. Remove the CAS 40 (or 10) from the guiding catheter 30 completely pulling it back into the insertion tube 60. Thus if the CAS 40 (or 10) needs to be put back into the body it is collapsed and ready to go.
23. When indicated, advance appropriate diagnostic electrophysiology catheters through the guiding catheter to confirm that the ablation has been successful.
24. Remove all remaining apparatus from the body.

A similar approach can be used with the CAS, via access from a peripheral artery such as the femoral artery, to treat hypertension, via ablation of tissue in the periostial aortic wall tissue surrounding one or both of the renal arteries, with the goal of ablating afferent and/or efferent sympathetic nerve fibers entering or exiting the kidney.

While the proximal end of the metallic injector tubes 15 and 45 shown here terminate in the injector manifold 11, it is also envisioned that these tubes could connect to wires that run to the proximal end of the CAS to allow the injector needles 19 and 49 to act as electrodes for sensing signals from the ostial wall of the target vessel as well as potentially delivering electrical stimulation or higher voltages and currents to ablate the tissue in the ostial wall by electrical or RF ablation.

Figure 10:
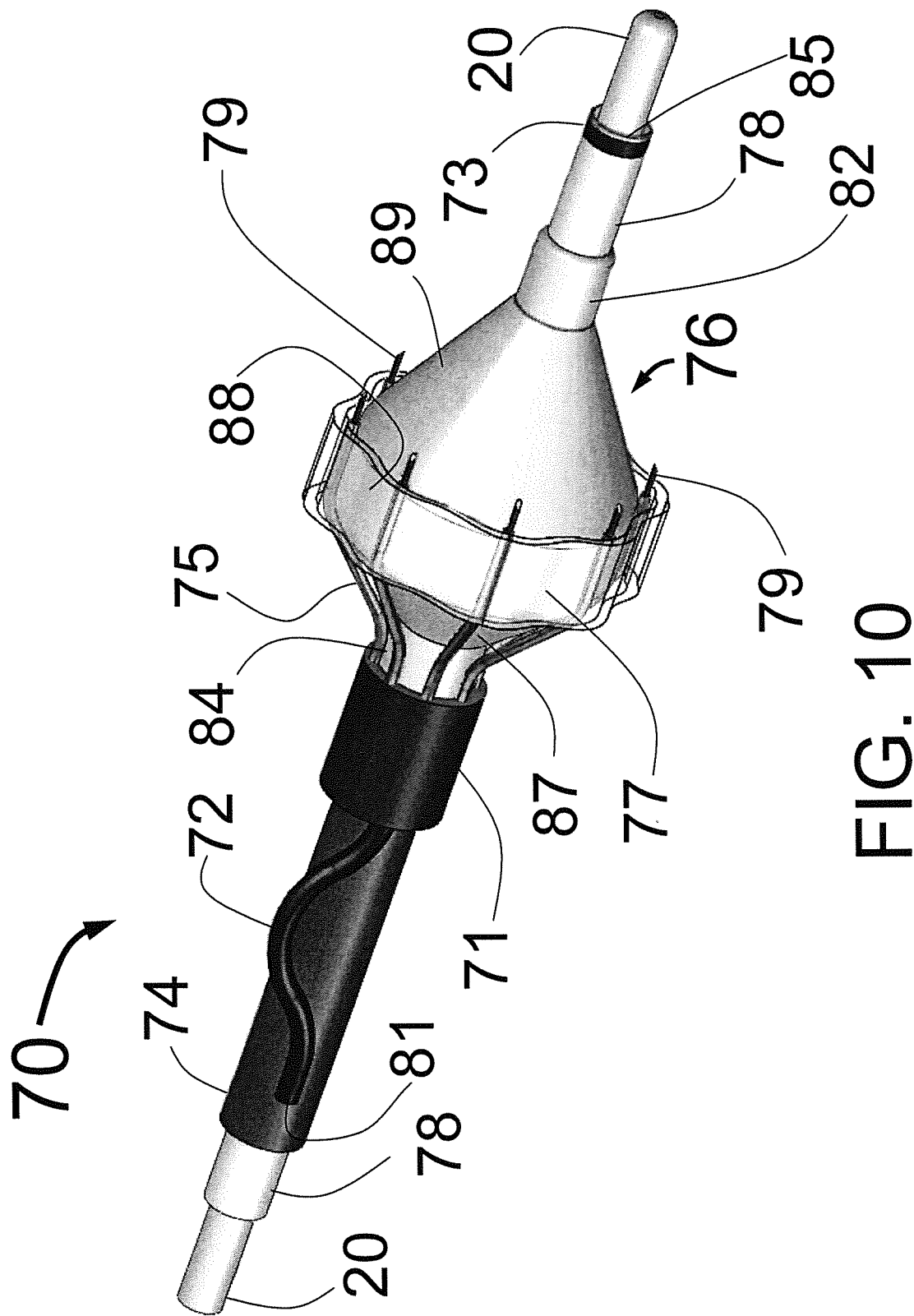
FIG. 10 is a three dimensional sketch of an other embodiment of the CAS that uses a balloon to expand the expandable injector tubes used to deliver the ablative substance to the ostial wall of the target vessel.

FIG. 10 is a three dimensional sketch of an other embodiment of the CAS 70 that uses a balloon 76 to expand the expandable injector tubes 75 used to deliver the ablative substance to the ostial wall of the target vessel through the injection needles 79. The 8 injector tubes 75 connect to the manifold 71 that is free to slide distally and proximally along the catheter outer tube 74 as the balloon 76 is inflated and deflated. The manifold 71 connects the lumens of the injector tubes 75 to the tube 72 with fluid injection lumen 81. The tube 72 connects to a fitting at the proximal end of the CAS 70 such as the Luer fitting 33 of FIG. 7. A source of ablative fluid would attached to the fitting and be used to inject the ablative fluid through the fluid injection lumen 81 of the tube 72 into the expandable tubes 75 and out the injection needles 79 into the ostial wall of the target vessel. The balloon 76 is inflated and deflated by delivery of a fluid through the lumen formed between the outer tube 74 and the inner tube 78. The proximal shaft 84 of the balloon 76 is attached to the outside of the outer tube 74 and the distal shaft 82 of the balloon 76 is attached to the outside of the inner tube 78. The inside of the inner tube 78 provides a guide wire lumen 85 for the guide wire 20. The distal end of the inner tube 78 includes a radiopaque marker 73 to assist in visualizing the distal end of the CAS 70 as it is inserted into the target vessel. The balloon 76 includes a distal shaft 82, a proximal shaft 84, a proximal conical section 87, a central cylindrical section 88, and a distal conical section 89. The injector tubes 74 are attached to the outside of the central cylindrical section 88 of the balloon 76 and are also held by the expandable band 77 that covers the outside of the injector tubes 75 and the central cylindrical section 88 of the balloon 76. While the expandable band 77 is shown in FIG. 10 as covering only the central cylindrical portion 88 of the balloon 76, it is envisioned that it might also extend in the proximal direction to cover the injector tubes 75 over their entire length proximal to the needles 79 which would make a smoother outer surface of the CAS 70 over this portion. The needles 79 extend in the distal direction from the distal end of the injector tubes 75 and may be made of a standard needle material such as stainless steel or a more radiopaque material such as tantalum or tungsten or plated with a radiopaque material such as gold or platinum. The expandable band 77 also serves the purpose for the CAS 70 of being the penetration limiting member located proximal to the distal end of each needle 70 that only allows each needle 70 to penetrate a preset distance into the ostial wall of the target vessel. In this embodiment the penetration limiting member 77 should limit needle penetration to a depth between 0.5 mm and 1 cm. It is also envisioned that the entire CAS 70 could be covered by a sheath (not shown) that would protect the needles 79 from coming into contact with the inside of the guiding catheter used to delivery the CAS 70 to the target vessel. The sheath would be slid back in the proximal direction once the CAS 70 is positioned with the guide wire 20 within the target vessel. The CAS 70 can also be used with an insertion tube 60 as shown in FIG. 9.

The balloon 76 can be either an elastic balloon or a semi-compliant or non-compliant balloon such as used in angioplasty catheters. Such a balloon is typically inflated with normal saline solution including a contrast agent.

It is also envisioned that the best way to protect the needles 79 of the CAS 70 would be to have an elastic band (not shown in FIG. 10) attached to the distal shaft of the balloon 82 or the inner tube 78 (or both) cover the distal ends of the needles 79 in the pre-deployment condition. Inflation of the Balloon 76 would pull the needles 79 in the proximal direction out from under such an elastic band. Such an elastic band would prevent the needles 79 from catching on the inside of the guiding catheter as the CAS 70 is advanced into the body.

For this embodiment of the CAS 70, the method of use would be the following steps:

1. Remove the sterilized CAS 70 from its packaging in a sterile field.
2. Flush the guide wire lumen 85 with saline solution.

Access to the left atrium via a large peripheral vein, such as the femoral vein, typically with the insertion of a sheath.

Use a trans septal approach to get into the left atrium, via the vein, to the right atrium, to enter the left atrium. This approach is a well known procedure.

Advance a guide wire and guiding catheter across the inter-atrial septum into the left atrium.

Using a guiding catheter or guiding sheath with a shaped distal end, engage the first targeted pulmonary vein. This can be confirmed with contrast injections as needed.

Advance a guide wire through the guiding catheter into the pulmonary vein.

Insert the proximal end of the guide wire 20 into the guide wire lumen 85 of the CAS and bring the wire 20 through the CAS 70 and out the proximal end Luer fitting 38 of FIG. 7.

Place the distal end of an insertion tube 60 of FIG. 9 which constrains the distal end of the CAS 70 into the proximal end of the guiding catheter. There is typically a Tuohy-Borst fitting attached to the distal end of a guiding catheter to constrain blood loss. The insertion tube 60 can be pushed through the opened Tuohy-Borst fitting and the Tuohy-Borst fitting closed on its outside to hole it in place.

Advance the distal end of the CAS 70 out of the insertion tube 60 and into the guiding catheter.

Advance the CAS 70 through the guiding catheter, and tracking over the guide wire 20, until the distal marker band 73 is located just proximal to the distal end of the guiding catheter.

Advance the CAS 70 over the guide wire 20 until the marker band 73 is within the target vessel and the distal shaft 82 of the balloon 76 is just proximal to the target vessel.

Pull the guiding catheter back so that the balloon 76 is now distal to the distal end of the guiding catheter.

Inflate the balloon 76 until it is the appropriate diameter which is between 1 and 10 mm larger in diameter than the target vessel.

Advance the CAS until the injector needles in the injector tubes 75 penetrate the ostial wall, with the penetration depth being a fixed distance limited by the expandable band 77. The distal conical section of the balloon 76 will act to center the CAS 70 as it is advanced into the target vessel.

Attach a syringe or injection system to the Luer fitting 35 of FIG. 7 that provides ablative fluid that will be injected into the ostial wall.

Engagement of the ostial wall could be confirmed by injection of a small volume of iodinated contrast via a syringe through the Luer fitting 35 and out of the needles 79 prior to injection of an "ablative" fluid such as alcohol. If there is contrast "staining" of the tissue this will confirm that the needles 79 are engaged into the tissue and not free floating in the left atrium or aorta.

Inject an appropriate volume of ethanol (ethyl alcohol) or other appropriate cytotoxic fluid from the syringe or injection system through the lumen 81 of the tube 82 and out of the needles 79 into the ostial wall. A typical injection would be 1-10 ml. This should produce a multiplicity of interlocking circles of ablation (one for each needle) that should intersect to form a ring around the ostium of the target vessel as is seen in FIG. 6E.

Deflate the balloon 76 and retract the CAS 70 back into the guiding catheter.

In some cases, one may rotate the CAS 70 between 20-90 degrees and then repeat the injection to make an even more definitive ring of ablation.

The same methods as per steps 6-20 can be repeated to ablate tissue around the one or more of the other pulmonary veins during the same procedure, as indicated to ensure AF ablation or the 2nd Renal artery in the treatment of hypertension.

Remove the CAS 70 from the guiding catheter completely pulling it back into the insertion tube 60. Thus if the CAS 70 needs to be put back into the body it is collapsed and ready to go.

When indicated, advance appropriate diagnostic electrophysiology catheters through the guiding catheter to confirm that the ablation has been successful.

Remove all remaining apparatus from the body.

A similar approach can be used with the CAS 70, via access from a peripheral artery such as the femoral artery, to treat hypertension, via ablation of tissue in the periostial aortic wall tissue surrounding one or both of the renal arteries, with the goal of ablating afferent and/or efferent sympathetic nerve fibers entering or exiting the kidney.

While the CAS 70 shows a separate tube 72 it is envisioned the fluid injection lumen of the CAS 70 catheter body could be constructed similar to that of the CAS 10 of FIGS. 1-5 where an additional outer tube would be placed with the fluid injection lumen being between the outer and middle tubes. It is also envisioned that instead of concentric tubes with lumens between the tubes, a multi-lumen catheter could be used with separate lumens formed during extrusion of the catheter body. Similarly, while the shape of the tubes and lumens shown here are cylindrical, other shapes are also envisioned.

While the present invention described here has an expandable balloon as a centering means, it is envisioned that a fixed diameter centering section could be used or a mechanical expandable structure could also facilitate centering of the CAS. While the version of the CAS shown here is an over the wire design, it is also envisioned that a rapid exchange guide wire system where the wire exits the catheter body at a location between the proximal end and the fluid injection ring would be feasible here. In addition, a fixed wire design such as that shown by Fischell et al in U.S. Pat. No. 6,375,660 for a stent delivery catheter would also work here.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A method of treating a target tissue, the method including:
   advancing an ablation system through a target vessel until a distal end of the ablation system lies near the target tissue, the ablation system including a distal portion with tubes and injection needles, the ablation system designed to allow injection of ablative fluid through the injection needles;
   centering the ablation system with respect to the target vessel by expanding an expandable structure of the ablation system outward with respect to a lumenal wall of the target vessel;
   causing the tubes and injection needles to expand outward around a circumference of the ablation system;
   advancing the injection needles at least partially through the lumenal wall of the target vessel and into the target tissue; and injecting ablative fluid into the target tissue through the injection needles.

2. The method of claim 1 wherein the ablative fluid comprises ethyl alcohol.

3. The method of claim 1 further including retracting the tubes into a body of the ablation system.

4. The method of claim 1 wherein the ablation system comprises at least 3 tubes and at least 3 injection needles.

5. The method of claim 1 wherein the expandable structure is a manually expandable structure and centering the ablation system includes manual expansion of the expandable structure.

6. The method of claim 1 wherein the expandable structure is self-expanding.

7. The method of claim 1 further including retracting the distal portion of the ablation system back into a guiding catheter.

8. The method of claim 1 further including limiting the penetration of the injection needles into the target tissue.

9. The method of claim 1 wherein the expandable structure comprises a balloon.

10. The method of claim 1 wherein the expandable structure is expanded to a diameter 1 mm to 4 mm less than the diameter of the target vessel.

11. The method of claim 1 wherein the target tissue is within the lumenal wall of the target vessel.

12. A method of treating a target tissue, the method including:
    advancing an ablation system through a target vessel until a distal end of the ablation system lies near the target vessel, the ablation system including a distal portion with tubes and injection needles, the ablation system designed to allow injection of ablative fluid through the injection needles;
    centering the ablation system with respect to the target vessel by expanding an expandable structure of the ablation system outward with respect to a lumenal wall of the target vessel;
    advancing the injection needles at least partially through the lumenal wall and into the target tissue; and
    injecting ablative fluid into the target tissue through the injection needles.

13. The method of claim 12 where the ablative fluid comprises ethyl alcohol.

14. The method of claim 12 further including retracting the tubes into a body of the ablation system.

15. The method of claim 12 wherein the ablation system comprises at least 3 tubes and at least 3 injection needles.

16. The method of claim 12 wherein the expandable structure is a manually expandable structure and centering the ablation system includes manual expansion of the expandable structure.

17. The method of claim 12 wherein the expandable structure is self-expanding.

18. The method of claim 12 further including retracting the distal portion of the ablation system back into a guiding catheter.

19. The method of claim 12 further including limiting the penetration of the injection needles into the target tissue.

20. The method of claim 12 wherein the expandable structure comprises a balloon.

21. The method of claim 12 wherein the expandable structure is expanded to a diameter 1 mm to 4 mm less than the diameter of the target vessel.

22. The method of claim 12 wherein the target tissue is within the lumenal wall of the target vessel.

\* \* \* \* \*

UNITED STATES PATENT AND TRADEMARK OFFICE
CERTIFICATE OF CORRECTION

| | |
|---|---|
| PATENT NO. | : 9,795,441 B2 |
| APPLICATION NO. | : 14/814962 |
| DATED | : October 24, 2017 |
| INVENTOR(S) | : David R. Fischell et al. |

Page 1 of 1

It is certified that error appears in the above-identified patent and that said Letters Patent is hereby corrected as shown below:

On the Title Page

Under (*) Notice Line 4:
Insert --This patent is subject to a terminal disclaimer--.

Signed and Sealed this
Twelfth Day of June, 2018

Andrei Iancu
*Director of the United States Patent and Trademark Office*